United States Patent [19]

Nielsen et al.

[11] Patent Number: 5,756,830
[45] Date of Patent: May 26, 1998

[54] PROCESS FOR PREPARING INTERMEDIATES FOR THE SYNTHESIS OF ANTIFUNGAL AGENTS

[75] Inventors: Christopher M. Nielsen, Mine Hill; Anantha Sudhakar, East Brunswick, both of N.J.

[73] Assignee: Schering Corporation, Kenilworth, N.J.

[21] Appl. No.: 766,441

[22] Filed: Dec. 12, 1996

Related U.S. Application Data

[60] Provisional application No. 60/008,909, Dec. 20, 1995.

[51] Int. Cl.$^6$ .......................... C07C 67/00; C07C 67/12
[52] U.S. Cl. ................................................. 560/239
[58] Field of Search ............................... 560/239

[56] References Cited

U.S. PATENT DOCUMENTS

| | | | |
|---|---|---|---|
| 3,923,865 | 12/1975 | Nelson | 260/468 D |
| 5,403,937 | 4/1995 | Saksena et al. | 548/268.8 |
| 5,442,093 | 8/1995 | Sudhakar | 560/82 |

FOREIGN PATENT DOCUMENTS

WO 93/22451  11/1993  WIPO.

OTHER PUBLICATIONS

Saksena et al. (1995) Tetrahedron Letters, 36(11) pp. 1787–1790.
Martinelle et al. (1995) Biochimica et Biophysica Acta, 1251, pp. 191–197.

*Primary Examiner*—Gary Geist
*Assistant Examiner*—Rosalynd Keys
*Attorney, Agent, or Firm*—Arthur Mann; Henry C. Jeanette

[57] ABSTRACT

A process for producing a crystalline chiral hydroxy ester of the formula:

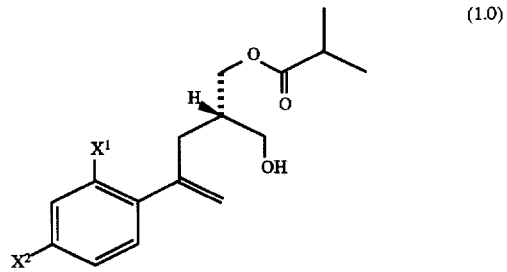

is disclosed.

The process comprises reacting a diol of the formula:

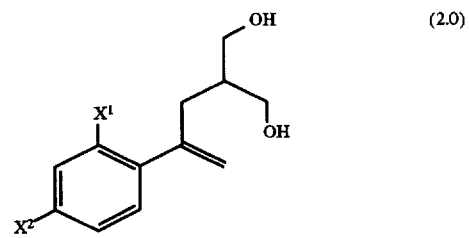

with an effective amount of isobutryic anhydride and an effective amount of a lipase enzyme in an effective amount of acetonitrile, said reaction being conducted at a low temperature, and wherein $X^1$ and $X^2$ are each independently selected from F or Cl.

17 Claims, No Drawings

PROCESS FOR PREPARING INTERMEDIATES FOR THE SYNTHESIS OF ANTIFUNGAL AGENTS

This application claims the benefit of U.S. provisional application No. 60/008,909, filed Dec. 20, 1995.

BACKGROUND OF THE INVENTION

U.S. Pat. No. 5,403,937, issued Apr. 4, 1995, and WO/94/25452, published Nov. 10, 1994, disclose a process for making intermediates for the synthesis of antifungal agents. It is disclosed that compounds of the formula:

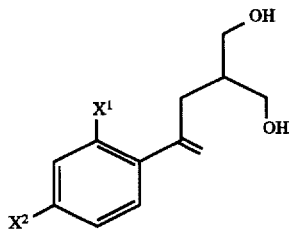

can be treated with a mild acylating agent, preferably an ester of the formula $R^1$—C(O)—$OR^3$ (wherein $R^1$ is $C_1$ to $C_6$ alkyl, aryl or —$(CH_2)_n CO_2 H$, wherein n is 1, 2, 3 or 4, and $R^3$ is trifluoroethyl, $C_1$-$C_6$ alkyl or $C_2$-$C_6$ alkenyl), most preferably vinyl acetate, in the presence of an enzyme, most preferably Novo SP435, in a suitable solvent, such as toluene or $CH_3CN$, at 0° to 35° C., preferably about 25° C., to form the chiral hydroxy ester of the formula:

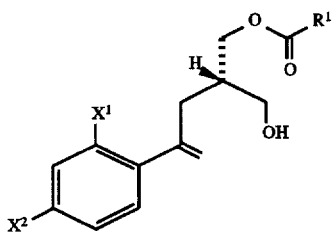

wherein $X^1$ and $X^2$ in the above formulas are independently F or Cl.

In view of the interest in obtaining chiral hydroxy esters in a large enantiomeric excess, a process for providing such esters would be a welcome contribution to the art. The invention described herein provides just such a process.

SUMMARY OF THE INVENTION

This invention provides a process for preparing the crystalline chiral hydroxy esters of Formula 1.0 by the stereoselective acylation of a diol of Formula 2.0 with isobutyric anhydride. The process comprises reacting a diol of Formula 2.0 with isobutyric anhydride and a lipase enzyme in a suitable organic solvent (e.g., acetonitrile) at a low temperature. A sufficient amount of enzyme and isobutyric anhydride is used to allow the reaction to proceed at a reasonable rate to the formation of the chiral hydroxy ester while keeping the formation of diesters to a minimum.

Thus, this invention is directed to a process for preparing a crystalline chiral hydroxy ester of the formula:

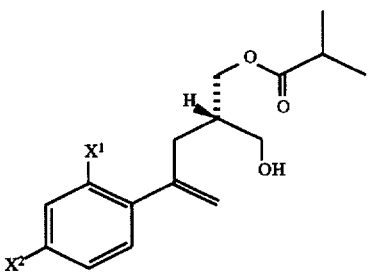

comprising reacting a diol of the formula:

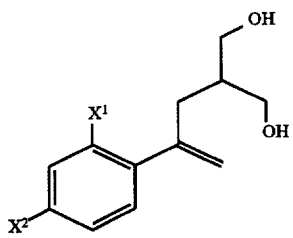

with an effective amount of isobutyric anhydride and an effective catalytic amount of a lipase enzyme in a suitable organic solvent, said reaction being conducted at a low temperature, and wherein $X^1$ and $X^2$ are each independently selected from F or Cl.

DETAILED DESCRIPTION OF THE INVENTION

The reaction of the diol (2.0) with isobutyric anhydride and the lipase enzyme is preferably conducted under an inert atmosphere, such as nitrogen. Also, it is preferred that the reaction be conducted under anhydrous conditions.

In the compounds of Formulas 1.0 and 2.0, $X^1$ and $X^2$ are each preferably F.

The diol of Formula 2.0 can be prepared according to the methods described in U.S. Pat. No. 5,403,937, issued Apr. 4, 1995, and WO/94/25452, published Nov. 10, 1994; the disclosures of each being incorporated herein by reference thereto.

The isobutyric anhydride (hereinafter "anhydride") is used in an effective amount, i.e., an amount which effectively provides the mono chiral hydroxy ester of Formula 1.0 while avoiding the formation of diester. If an insufficient amount of anhydride is used the desired enantiomeric excess (hereinafter "e.e.") is not obtained. If an unquenched excess of anhydride is used then larger amounts of diester are formed.

Generally, at least about one mole equivalent (Meq) of anhydride is used, with about 1 to about 1.1 Meq being preferred, and about 1.05 to about 1.1 Meq being more preferred, and about 1.1 Meq being most preferred.

An excess of anhydride (i.e., an amount greater than 1.1 Meq) can be used provided that a suitable quenching reagent is added to the reaction mixture as soon as the desired e.e. is obtained. The quenching reagent stops the reaction by reacting with the remaining anhydride. Thus, the anhydride can be used in an amount of about 1 Meq to about 3 Meq, provided that when amounts greater than 1.1 Meq are used a suitable quenching reagent is added to the reaction mixture as soon as the desired e.e. is obtained—i.e., as soon as an e.e. of about 97 to about 100% is obtained. The quenching reagent is added in a sufficient amount to react with (i.e., consume) the remaining anhydride so as to stop the reaction. Suitable quenching reagents include but are not limited to water and alcohols (e.g., a $C_1$ to $C_3$ alkanol, such as methanol, ethanol, propanol or isopropanol).

The lipase enzyme used is one that can catalyze the esterification of a symmetrical prochiral diol (e.g., Formula 2.0), such that a single chiral hydroxy ester (e.g., Formula 1.0) is formed in high e.e. The preferred enzyme preparation to produce the S-monoester was commercially available under the product designation NOVO SP435 (Candida antartica, Novozym 435 from Novo Nordisk). Those skilled in the art will appreciate that this is an immobilized form of Candida antartica. This enzyme is reported to be a triacylglycerol hydrolase (E.C. no. 3.1.1.3) and at the same time it acts as an effective carboxylesterase.

The enzyme is used in an effective catalytic amount—i.e., an amount which effectively catalyzes, at a reasonable rate of reaction, the esterification of the diol of Formula 2.0 to the hydroxy ester of Formula 1.0. Those skilled in the art will appreciate that the enzyme can be used in amounts of about 1 to about 100 wt % (relative to the charge of diol 2.0). Generally, the enzyme is used in amounts of about 1 to about 25 wt %, with about 1 to about 10 wt % being preferred, and about 3 to about 7 wt % being more preferred, and about 5 wt % being most preferred.

Suitable organic solvents include but are not limited to THF (tetrahydrofuran), ethyl acetate, acetonitrile, toluene and methylene chloride. Preferably, acetonitrile is used. It will be appreciated by those skilled in the art that the solvent is used in an amount which effectively dissolves the reactants and allows the reaction to proceed at a reasonable rate. For example, a solvent, such as acetonitrile, can be used in an amount of at least about 5 wt volumes (i.e., a volume that is in an excess of at least 5 times (5X) the amount of diol 2.0), with about 5 wt volumes being preferred.

Acetonitrile may contain residual water (e.g., about 0.03 to about 0.05%) which could react with the anhydride. The amount of anhydride used takes into consideration any water that may be present in the acetonitrile. For example, the use of 1.1 Meq of anhydride takes into consideration the reaction of about 0.05 Meq of anhydride with residual water in the acetonitrile and the reaction of about 1.05 Meq of anhydride with the diol 2.0.

The reaction is conducted at a temperature low enough to reduce the formation of unwanted by-products, but not so low as to require an unreasonably long reaction time. A suitable temperature is about −15° to about +5° C., with about −15° to about 0° C. being preferred.

If desired the hydroxy ester 1.0 can be isolated by techniques well known to those skilled in the art. For example, isolation can be accomplished using an aqueous bicarbonate and water work-up followed by solvent replacement, in vacuo, with heptane.

The examples that follow are intended to exemplify the claimed invention, and should not be construed as limiting the disclosure or the claimed invention.

EXAMPLE 1

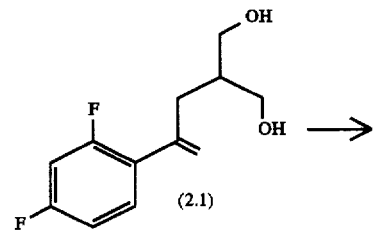

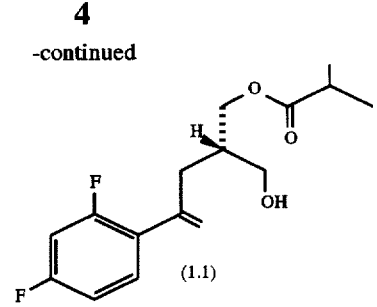

Under nitrogen, the diol 2.1 (80 g) was dissolved in 400 ml (5 volumes) of dry acetonitrile. To this solution, 58.9 g of sodium bicarbonate and 4.0 g of Novozym SP 435 were added and the mixture was cooled to a temperature between −10° and −15° C. When the mixture was cool, 62.88 g of 97% pure isobutyric anhydride was charged to the stirring solution while maintaining the temperature. After stirring isothermally for about 20 hours, the desired e.e. % was obtained along with a diester level of about 4%. The reaction was filtered through celite and the filter cake was washed with two 25 ml portions of acetonitrile. The solution was diluted with 800 ml (10 volumes) of methyl t-butyl ether and then washed with three successive 600 ml portions of 5% aqueous bicarbonate and twice with successive 600 ml portions of deionized water until the final pH was between 6.5 and 7. The solution was concentrated in vacuo followed by solvent replacement with heptane in vacuo to give a slurry of white solid in heptane. The volume was brought to 750 ml (9 volumes) with heptane. This mixture was heated to 50° C. to 60° C. give a solution. A thick slurry was obtained by cooling slowly to ambient temperature, followed by cooling in an ice/acetone bath to −12° C. After stirring for 30 minutes, the product was isolated by vacuum filtration and washed with 80 ml (1 volume) of −10° C. heptane. This yielded, after vacuum drying at ambient temperature, the hydroxy ester 1.1, 95.3 g (91% of theory) of white needles that had a purity of 99% and a corrected e.e. % of 99.4%. Corrected ee. %=(S-ester %−R-ester %)/(S-ester %+R-ester %+diol 2.1). An additional 5 g of the hydroxy ester 1.1 (5% of theory, corrected e.e. %=97.9%) was isolated from the mother liquors by concentration and filtration. $^1$H-NMR (400 MHZ, CDCl$_3$): δ 7.53–7.47 (m, 1H), 6.91–6.86 (m, 1H), 6.83–6.78 (m, 1H), 4.17–4.13 (dd, 1H), 4.09–4.04 (m, 2H), 3.87–3.84 (dd, 1H), 3.69 (s, 2H), 2.59–2.53 (m, 3H), 2.19–2.12 (dd, 1H), 1.17 (s, 3H), 1.15 (s, 3H).

EXAMPLE 2

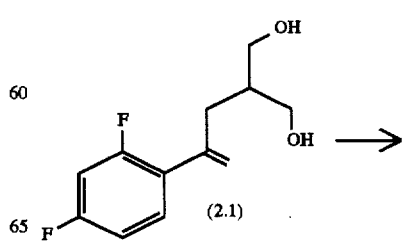

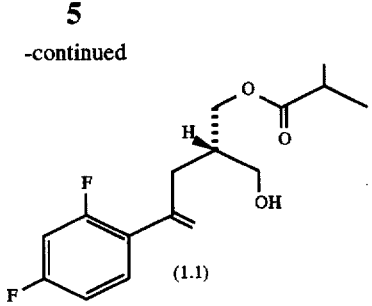

Under nitrogen, the diol (2.1), 8 Kg, was dissolved in 40 liters (5X) of acetonitrile. The resulting mixture showed 0.9% water by Karl Fischer analysis. This corresponds to 8 mol % water. Sodium bicarbonate USP, 5.6 Kg, was charged and the solution was cooled to about −10° C. Novozyme SP 435, 400 grams, was charged to the cooled solution. Isobutyric anhydride, 5.92 Kg (1.1 equivalents), was charged and the reaction mixture was stirred overnight at about −10° C. After 16 hours, the enzymatic acylation yielded a mixture that had an e.e. % of 98.3% and contained 4% diester and 0.6% diol (2.1).

HPLC analysis performed using a Chiralpak AS column (4.6 mm×250 mm), 5% ethanol in heptane as the solvent, a flow rate of 1 mL per minute, and a detector set to a wavelength of 215 nm yielded the following results for a sample taken at 16 hours: 0.4% starting material; 3.9% diester; 94.8% S-ester; and 0.8% R-ester.

EXAMPLE 3

COMPARATIVE EXAMPLE

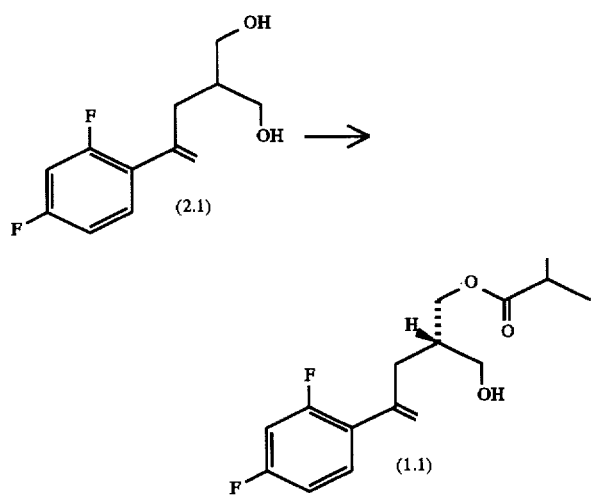

Under nitrogen, the diol (2.1), 33 kg, was dissolved in 165 liters of acetonitrile. Novozyme SP 435, 1.65 Kg, was charged to the solution and the reaction mixture was cooled to between about 0° to about 5° C. Vinyl acetate, 19.8 Kg, was added to the agitating solution. After 4.5 hours, the enzyme was removed from the reaction mixture by filtration through a sparkler.

The reaction was monitored by HPLC using a Chiralpak AS column (4.6 mm×250 mm), 5% ethanol in heptane as the solvent, a flow rate of 1 mL per minute, and a detector set to a wavelength of 215 nm. At 4.5 hours, HPLC yielded the following results: 0.4% starting material; 31.0% diester; 68.0% S-ester; 0.5% R-ester; and an e.e. % of 98.4.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for producing a crystalline chiral hydroxy ester of the formula:

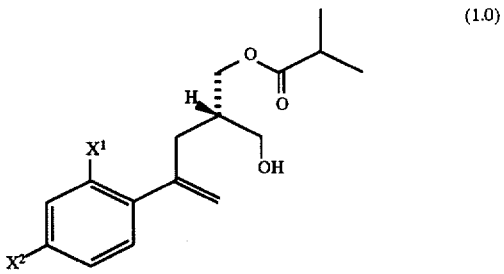

comprising reacting a diol of the formula:

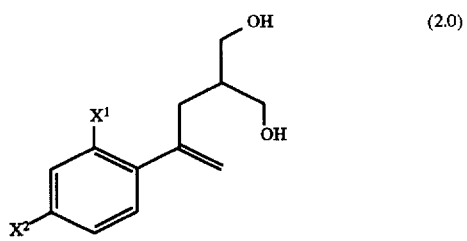

with an effective amount of isobutyric anhydride and an effective catalytic amount of a lipase enzyme in a suitable organic solvent, said reaction being conducted at a low temperature, and wherein $X^1$ and $X^2$ are each independently selected from F or Cl.

2. The process of claim 1 wherein $X^1$ and $X^2$ are F.

3. The process of claim 1 wherein said isobutyric anhydride is used in amounts of about 1.05 to about 1.1 Meq.

4. The process of claim 1 wherein the enzyme used is NOVO SP435.

5. The process of claim 4 wherein said enzyme is used in amounts of about 3 to about 5 wt % based on the charge of diol 2.0.

6. The process of claim 1 wherein said organic solvent is acetonitrile.

7. The process of claim 1 wherein the reaction is conducted at a temperature of about −15° to about +5° C.

8. The process of claim 1 wherein the reaction is conducted at a temperature of about −15° to about 0° C.

9. The process of claim 1 wherein the enzyme used is NOVO SP435, and the reaction is conducted at a temperature of about −15° to about +5° C.

10. The process of claim 9 wherein the enzyme is used in amounts of about 3 to about 7 wt % based on the charge of diol 2.0, and the isobutyric anhydride is used in amounts of about 1.05 to about 1.1 Meq.

11. The process of claim 10 wherein the organic solvent is acetonitrile.

12. The process of claim 11 wherein the enzyme is used in an amount of about 5 wt % based in the charge of diol 2.0.

13. The process of claim 12 wherein the reaction is conducted at a temperature of about −15° to about 0° C.

14. The process of claim 10 wherein $X^1$ and $X^2$ are F.

15. The process of claim 11 wherein $X^1$ and $X^2$ are F.

16. The process of claim 12 wherein $X^1$ and $X^2$ are F.

17. The process of claim 13 wherein $X^1$ and $X^2$ are F.

* * * * *